(12) United States Patent
Tan

(10) Patent No.: US 9,717,887 B2
(45) Date of Patent: Aug. 1, 2017

(54) CATHETER ASSEMBLY BLOOD CONTROL DEVICE AND RELATED METHODS

(71) Applicant: B. BRAUN MELSUNGEN AG, Melsungen (DE)

(72) Inventor: Soo Yong Tan, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 145 days.

(21) Appl. No.: 14/550,423

(22) Filed: Nov. 21, 2014

(65) Prior Publication Data

US 2015/0151089 A1   Jun. 4, 2015

Related U.S. Application Data

(60) Provisional application No. 61/911,939, filed on Dec. 4, 2013.

(51) Int. Cl.
| | | |
|---|---|---|
| *A61M 25/06* | (2006.01) | |
| *A61M 25/00* | (2006.01) | |
| *A61M 39/06* | (2006.01) | |

(52) U.S. Cl.
CPC .... *A61M 25/0693* (2013.01); *A61M 25/0097* (2013.01); *A61M 39/06* (2013.01); *A61M 39/0693* (2013.01); *A61M 25/0606* (2013.01); *A61M 2039/064* (2013.01); *A61M 2205/7536* (2013.01)

(58) Field of Classification Search
CPC .... A61M 2039/064; A61M 2205/7536; A61M 25/0097; A61M 25/0606; A61M 25/0693; A61M 39/06; A61M 39/0693; A61M 39/00; A61M 2039/0036
See application file for complete search history.

(56) References Cited

U.S. PATENT DOCUMENTS

| | | | |
|---|---|---|---|
| 4,588,403 A * | 5/1986 | Weiss | A61M 5/162 604/411 |
| 4,917,671 A | 4/1990 | Chang | |
| 4,935,010 A * | 6/1990 | Cox | A61M 39/045 604/122 |
| 5,817,069 A * | 10/1998 | Arnett | A61M 39/26 251/149.1 |
| 6,139,534 A * | 10/2000 | Niedospial, Jr. | A61J 1/2096 604/403 |

(Continued)

*Primary Examiner* — Quynh-Nhu H Vu
(74) *Attorney, Agent, or Firm* — Klein, O'Neill & Singh, LLP

(57) ABSTRACT

A catheter assembly includes a catheter hub and an introducer needle. The introducer needle extends through the catheter hub and through a catheter tube so as to assist placement of the catheter tube into a patient's blood vessel. Blood flashback into the catheter tube and/or catheter hub can indicate when the catheter tube is properly positioned within the blood vessel. After proper catheter tube placement is confirmed through blood flashback, the introducer needle is withdrawn. A septum blocks flashback blood from flowing proximally out of the catheter hub. One or more air vents enable air within the hub to vent when flashback blood enters the catheter hub. A porous hydrophobic material covers the one or more air vents. The hydrophobic material allows the air to flow therethrough and through the vents, but repels blood, blocking blood from flowing through the air vents.

9 Claims, 6 Drawing Sheets

(56) References Cited

U.S. PATENT DOCUMENTS

| | | | |
|---|---|---|---|
| 6,347,711 B1 * | 2/2002 | Goebel | A61M 5/38 |
| | | | 210/436 |
| 6,592,564 B2 | 7/2003 | Finch et al. | |
| 6,695,820 B1 | 2/2004 | Armstrong et al. | |
| 8,298,196 B1 | 10/2012 | Mansour | |
| 2008/0132877 A1 * | 6/2008 | McKinnon | A61M 39/045 |
| | | | 604/500 |
| 2013/0090610 A1 | 4/2013 | Stout et al. | |
| 2013/0289527 A1 | 10/2013 | Ravenscroft | |
| 2014/0276462 A1 | 9/2014 | Vincent et al. | |

* cited by examiner

CATHETER ASSEMBLY BLOOD CONTROL DEVICE AND RELATED METHODS

CROSS-REFERENCE TO RELATED APPLICATIONS

The application claims priority to U.S. Provisional Application No. 61/911,939, which was filed on Dec. 4, 2013, the entirety of which is hereby incorporated by reference.

BACKGROUND

The present disclosure relates to the field of infusion devices, and more particularly to peripheral intravenous (IV) catheters.

A catheter assembly for an IV catheter generally includes a flexible catheter, or catheter tube, coupled to a distal end of a catheter adapter, which can include a catheter hub. The catheter adapter retains the catheter tube so that other components can interact with the catheter tube. In order to place the catheter tube in the patient's blood vessel, an introducer needle is coupled to the catheter adapter so that the needle extends through the catheter adapter and catheter tube, with the sharp distal tip of the needle positioned just beyond the distal end of the catheter tube. The clinician uses the introducer needle to penetrate the patient's tissue and place the distal end of the catheter tube in a blood vessel.

Once the needle tip and the catheter tube are in the vessel, the clinician typically uses blood flashback to confirm that placement is correct. For example, when the needle tip and/or the catheter tube is properly placed in the vasculature of the patient, blood from the vessel may flow through the needle and/or the catheter tube into the catheter adapter. When the clinician sees the blood in the catheter adapter, the clinician knows that the distal tip of the needle and/or the distal end of the catheter tube is in place in the blood vessel.

It is generally desired that blood flashback flow be contained within the catheter adapter. Often, an elastomeric septum in the catheter adapter creates a seal to contain the blood in a distal chamber of the catheter adapter. However, in some instances the seal may lead to excessive positive air pressure in the catheter adapter or head pressure in an enclosed space, which positive air pressure may hinder or prevent blood flow into the catheter adapter. Thus, even though the catheter tube may be correctly placed, blood flashback may be less prominent, delayed, or prevented altogether. To relieve such positive air pressure, some prior catheter assemblies employ air vents that can direct air from the distal chamber past the sealed septum. However, air vents are vulnerable to leaking blood.

Once it is verified that the catheter tube is correctly placed in the blood vessel, the introducer needle is removed, and a source of IV fluids can be attached to the catheter adapter via a coupler such as a luer or threaded coupler. It is desirable to have a structure in which blood that may accumulate in the catheter adapter can be effectively flushed out of the catheter adapter by IV fluids once such fluids are attached.

SUMMARY

Accordingly, there is a need in the art for a catheter adapter that allows air to vent around a seal in order to facilitate blood flashback into the catheter adapter, but which minimizes or blocks blood leaking around the seal through such vents. There is also a need in the art for such a catheter adapter that allows for IV fluids to flush blood that may accumulate in the catheter adapter.

In accordance with one embodiment, the present disclosure provides a catheter assembly, comprising a catheter adapter having a distal end and a proximal end, an elongated catheter tube extending from the catheter adapter distal end, and distal and proximal chambers defined within the catheter adapter. The distal chamber communicates with the catheter tube. A divider is interposed between the distal chamber and the proximal chamber. One or more vent channels extend between the distal chamber and the proximal chamber so as to communicate the distal chamber with the proximal chamber. A hydrophobic porous material is interposed between the distal chamber and the one or more vent channels. The hydrophobic porous material is configured to allow air to pass therethrough so that air from the distal chamber can flow through the one or more vent channels to the proximal chamber. The hydrophobic porous material is configured to repel blood so that blood within the distal chamber is prevented from flowing through the one or more vent channels.

In some embodiments, the one or more vent channels can be formed through the divider. In further embodiments, the divider can comprise a central wall comprising an aperture, and a septum seat can be defined about the aperture. An elastomeric septum can be received within the septum seat so as to maintain a seal with the central wall. The one or more vent channels can formed through the central wall.

Some embodiments can additionally comprise a distal tube extending distally from the central wall and defining a fluid flow passage within the distal chamber. A distal side chamber can be defined between an outer surface of the distal tube and an inner surface of the catheter adapter. Side apertures can be formed through a wall of the distal tube and can communicate the fluid flow passage with the distal side chamber. The one or more vent channels can open into the distal side chamber.

In still further embodiments, the side apertures through the wall of the distal tube can be filled with the hydrophobic porous material, and the distal side chamber can comprise an air chamber. In additional embodiments, an inner surface of the distal tube can be coated with the hydrophobic porous material.

In yet additional embodiments, an inner surface of the distal tube can be coated with the hydrophobic porous material so that the hydrophobic porous material covers the side apertures.

In still additional embodiments, the side apertures through the wall of the distal tube can be open for both air and fluid to flow into the distal side chamber. In some such embodiments, the hydrophobic porous material can be applied to a distal side of the central wall so as to cover a distal opening of the one or more vent channels. In further embodiments, the side apertures through the wall of the distal tube can comprise a proximal side aperture and a distal side aperture, the distal side aperture being spaced distally from the proximal side aperture.

In yet further embodiments, the divider can comprise an elastomeric septum. In additional embodiments the one or more vent channels can be formed in a body portion of the catheter adapter, and the one or more vent channels can be at least partially filled with the hydrophobic porous material.

In accordance with another embodiment, a medical method is provided. The medical method comprises placing a distal end of a catheter tube in a patient blood vessel so that blood from the vessel is directed through the catheter tube and into a distal chamber of a catheter adapter coupled to the catheter tube. A portion of air within the distal chamber is displaced by blood from the vessel entering the distal chamber so that the portion of air flows from the distal chamber through a hydrophobic porous material and through a vent channel. Blood from the vessel is repelled by the hydrophobic porous material so as to be blocked by the hydrophobic porous material from flowing into the vent channel. The hydrophobic porous material is configured to allow air to pass therethrough but to repel blood.

In some embodiments, the catheter adapter can comprise a divider interposed between the distal chamber and a proximal chamber. Some embodiments additionally comprise directing a flow of fluid through an aperture in the divider into the distal chamber and flushing blood out of the chamber and back into the patient blood vessel.

In additional embodiments, the portion of air can flow through the vent channel and into the proximal chamber. In some such embodiments, the portion of air can flow through the hydrophobic porous material prior to flowing through the vent channel. In additional such embodiments, the portion of air can flow simultaneously through the hydrophobic porous material and through the vent channel.

DESCRIPTION

Figure 1:
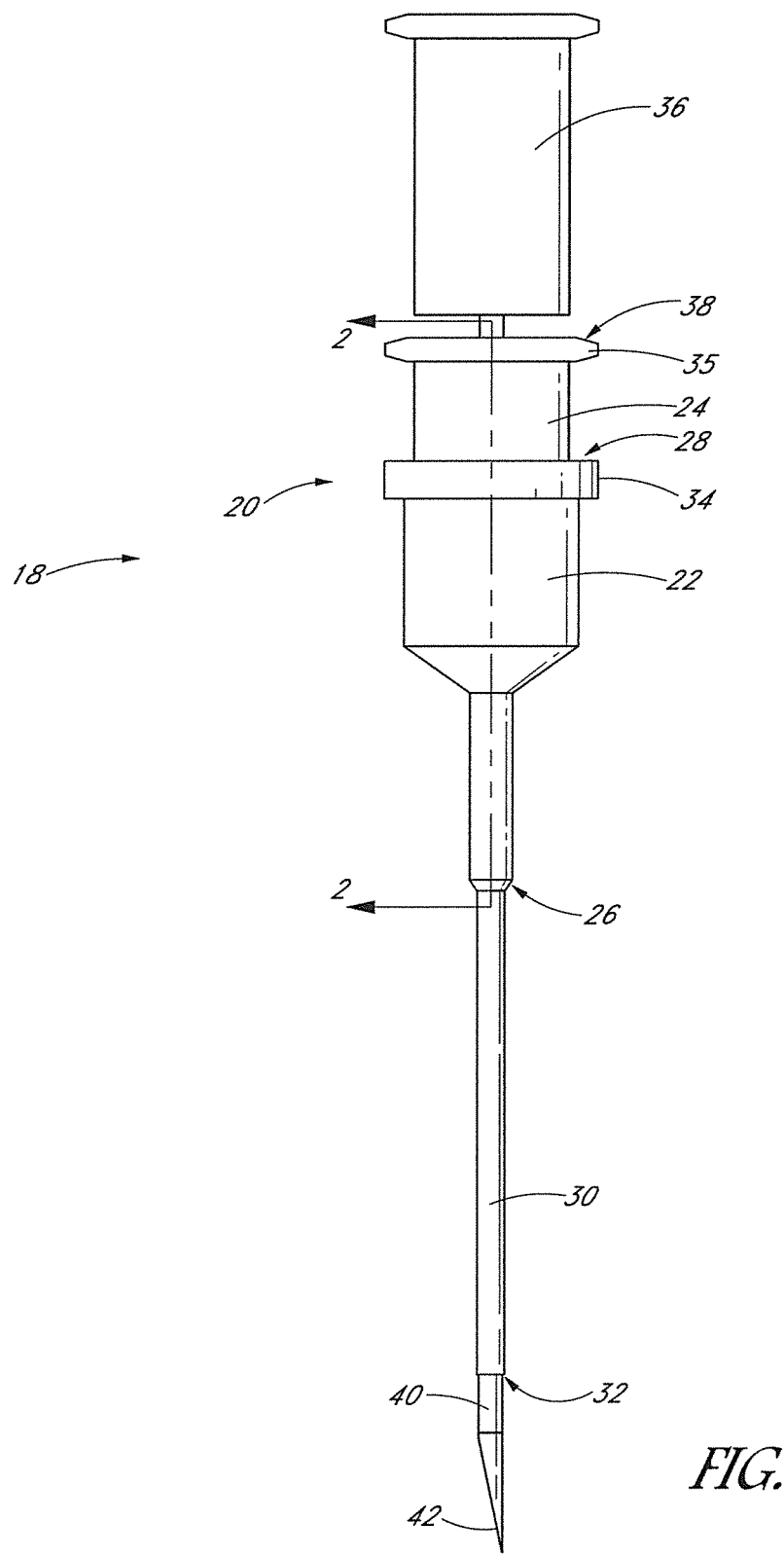
FIG. 1 shows a schematic view of a catheter assembly having features in accordance with the present disclosure.
Figure 2:
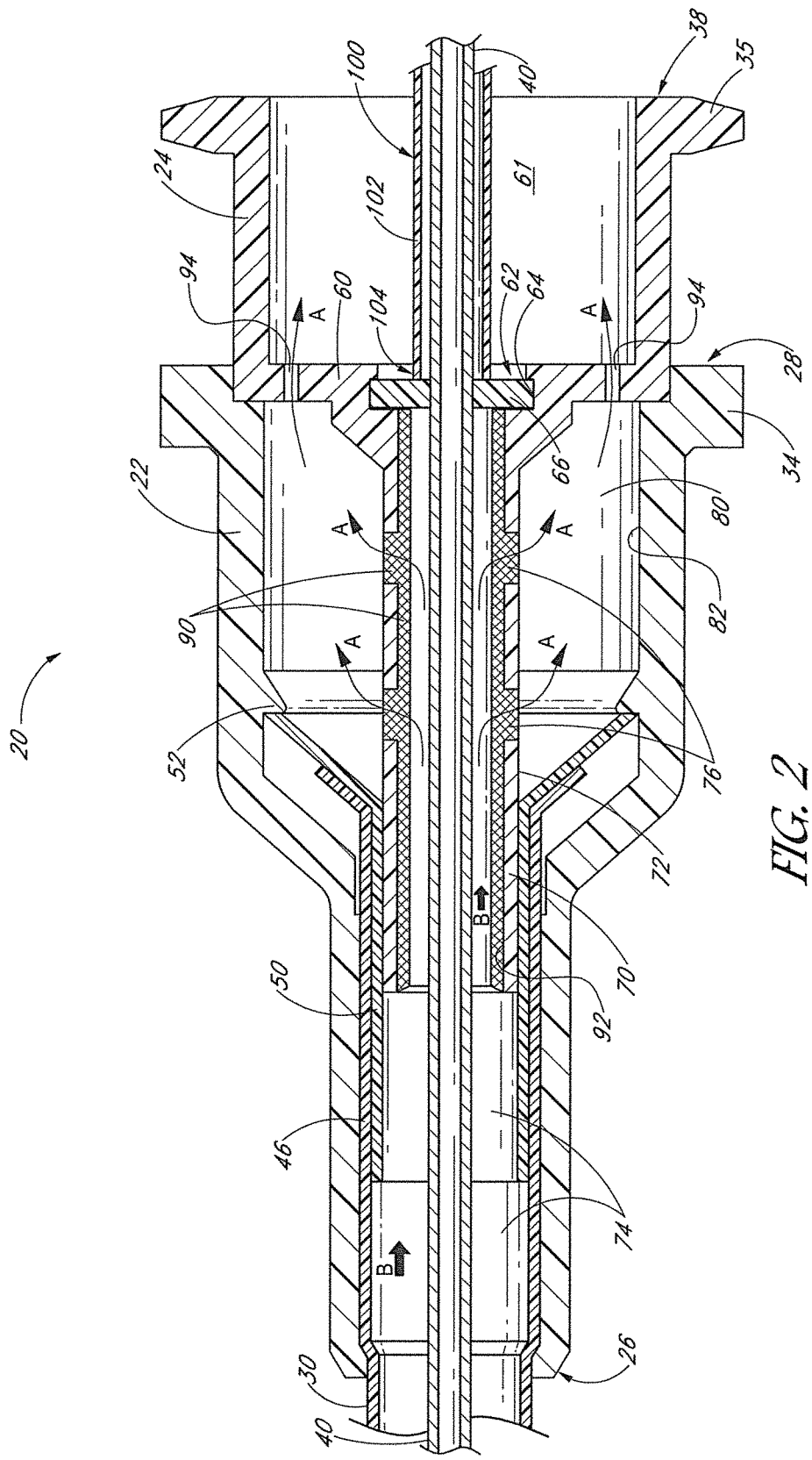
FIG. 2 is a cross-sectional view taken along lines 2-2 of FIG. 1.

With initial reference to FIGS. 1 and 2, an embodiment of a catheter assembly 18 includes a catheter adapter 20 made up of a catheter hub 22 and a septum hub 24. The catheter hub 22 has a distal end 26 and a proximal end 28. A catheter tube 30 extends distally from the catheter hub 22 and terminates at a distal end 32. In the illustrated embodiment, the septum hub 24 is attached to the proximal end 28 of the catheter hub 22. It is to be understood that the septum hub 24 can be attached to the catheter hub 22 in various ways, including, for example, being threaded or ultrasonically welded onto a proximal flange 34. In additional embodiments, the septum hub 24 can be integrally incorporated into the catheter hub 22 so that the catheter adapter 20 is a single piece.

With continued reference to FIGS. 1-2, a needle hub 36 can be arranged at or adjacent the proximal end 38 of the septum hub 24. Preferably, a hollow introducer needle 40 is attached to the needle hub 36 and extends through the catheter adapter 20 into and through the catheter tube 30, terminating at a distal tip 42 that is positioned just distal of the catheter tube distal end 32. In the illustrated embodiment, the needle hub 36 is not attached to the proximal end 38 of the septum hub 24. In other embodiments, however, a needle hub can be releasably attached to the septum hub. For example, in some additional embodiments, a proximal flange 35 at the proximal end 38 of the septum hub 24 can be threaded and/or configured to accept a connector, such as a luer-type connector or threaded connector, so as to releasably accommodate other components, such as a needle hub or a coupler for coupling IV fluid tubing, as desired.

Details of the illustrated needle hub 36 are not shown in the illustrated embodiment. It is to be understood, however, that needle hubs of various types and configurations may be employed. For example, needle hubs having uncomplicated configurations in which the needle hub simply supports an introducer needle may be employed, as can needle hub configurations having more complex structures such as needle tip covers and spring-loaded needle retractors.

Continuing with reference specifically to FIG. 2, a base 46 of the catheter tube 30 is disposed within the catheter hub 22. A catheter retainer 50 engages the catheter tube base 46 and a circumferential ridge 52 of the catheter hub 22 so as to securely hold the catheter tube 30 to the catheter hub 22.

The septum hub 24 includes a central wall 60. A proximal chamber 61 is defined by the septum hub 24 proximally of the central wall 60. A central aperture 62 is formed through the central wall 60, and a septum seat 64 is formed at and around the central aperture 62. An elastomeric septum 66 is configured to engage the seat 64 so as to establish a seal, thus sealing the central aperture 62. Preferably the septum 66 includes one or more slits 68 (see FIG. 3). When the septum 66 is at rest, the slit preferably closes so as to maintain the seal. As illustrated in FIG. 2, however, the introducer needle 40 can be extended through the slit 68. Preferably, the septum 66 will contact or press against the outer surface of the needle 40 so as to maintain a full or partial seal around the needle.

An elongated distal tube 70 extends distally from the central wall 60 and is aligned with the central aperture 62. An outer surface 72 of the elongated distal tube 70 along a distal portion thereof engages the catheter retainer 50, preferably in a manner that creates a full or partial seal between the outer surface 72 and the retainer 50. Also, the distal tube 70 opens into a distal flow passage 74 defined within the catheter hub 22.

One or more side apertures 76 are formed through the elongated distal tube 70 proximal of the catheter retainer 50. The side apertures 76 open into a distal side chamber 80 defined within the catheter hub 22 between the catheter retainer 50, the outer surface 72 of the distal tube 70, the inner surface 82 of the catheter hub 22 and a distal face of the central wall 60. In the illustrated embodiment, a distal pair of opposing ones of the side apertures 76 are spaced distally from a proximal pair of opposing ones of the side apertures 76. Air vents 94, or vent channels, are formed in the central wall 60 and preferably are positioned so as to communicate the distal side chamber 80 with the proximal chamber 61.

Continuing with reference to FIG. 2, a hydrophobic porous layer or membrane 90 preferably is deposited on an inner surface 92 of the elongated distal tube 70. Preferably, the hydrophobic porous layer 90 fills the side apertures 76. In the illustrated embodiment the lumen diameter for the inner surface 92 of the elongated distal tube 70 is no less than the lumen diameter of the catheter tube 30, and does not limit the flow rate of IV fluids delivered to the patient through the catheter tube.

The hydrophobic porous layer 90 preferably is configured to allow air to flow therethrough, but to repel water-based substances such as blood. The porous layer 90 can be made from any of a number of suitable materials well known to those skilled in the art, such as super hydrophobic polyvinyldiflouride (PVDF). Thus, as best depicted in FIG. 2, during blood flashback, when blood B flows into the catheter hub 22, air A within the catheter hub 22 will be pushed by the blood flow B through the hydrophobic porous layer 90, through the side apertures 76 and into the distal side chamber 80. A portion of such airflow A can continue through the air vents 94 and into the proximal chamber 61 defined proximal of the central wall 60. Since the hydrophobic porous layer 90 repels blood, the blood B does not pass through the side walls 76. As such, the distal side chamber 80 remains blood free, and the air vents 94 readily enable air A displaced by blood B to vent out of the sealed portion of the catheter hub 22 distal of the septum 66, thus relieving air pressure that could otherwise build up in the distal flow passage 74, which pressure buildup could resist, delay or prevent flashback blood flow B into the distal flow passage 74.

Figure 3:
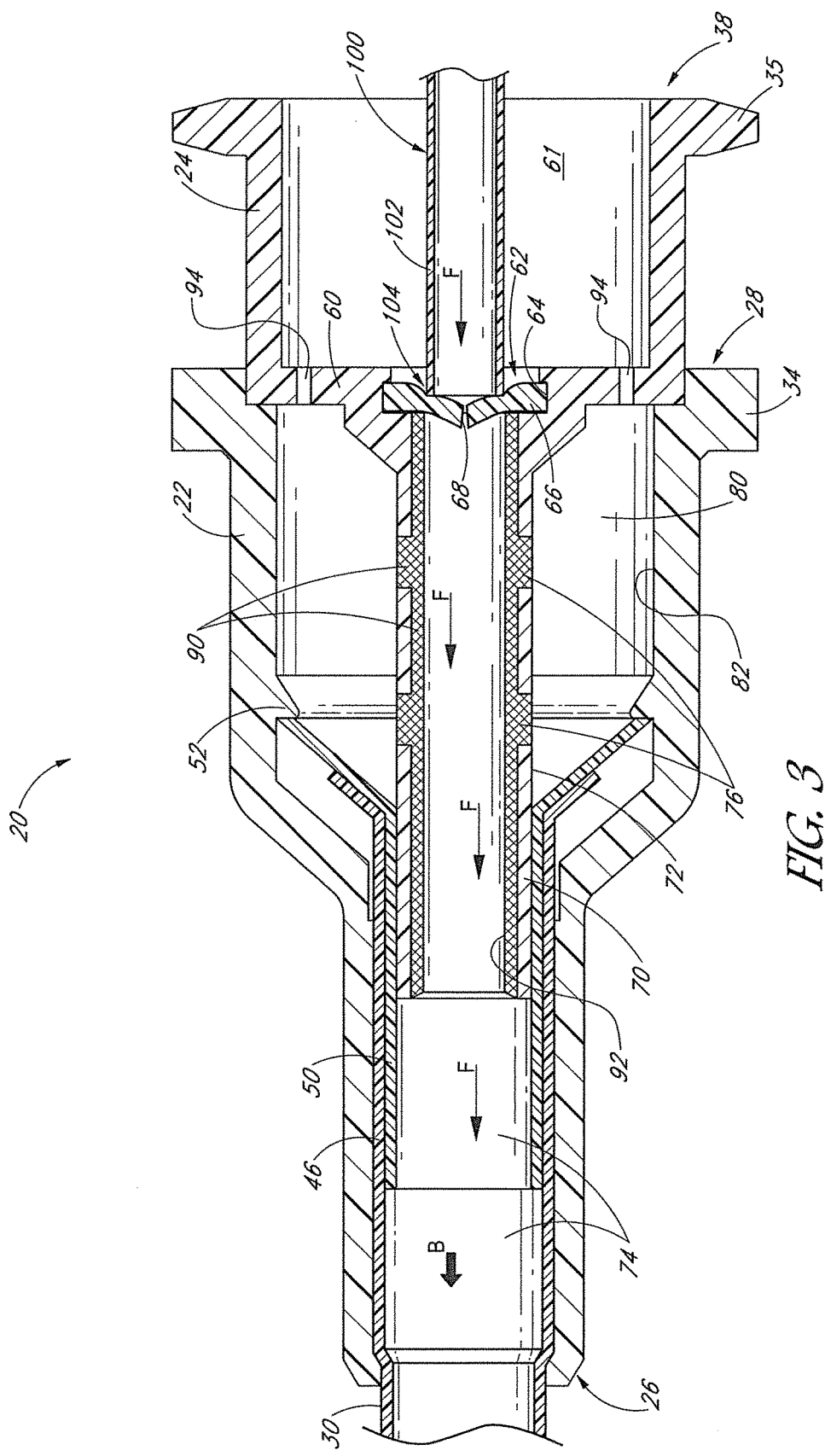
FIG. 3 shows the assembly of FIG. 2 with the needle withdrawn and IV fluid being delivered.

With continued reference to FIG. 2 and additional reference to FIG. 3, in the illustrated embodiment, a septum activator 100 can have an elongated hollow body 102, which terminates at a distal end 104. The illustrated septum activator 100 is positioned proximal of the septum 66 so that the distal end 104 of the elongated body 102 is immediately proximal of the septum 66.

In use, and as discussed above, once the distal end of the catheter tube 30 is confirmed by blood flashback to be positioned within a blood vessel lumen, the introducer needle 40 is withdrawn proximally. Flashback blood B remains within the distal flow passage 74. In a preferred embodiment, the septum activator 100 is moved distally a distance sufficient to engage and deform the septum 66 as depicted in FIG. 3. As such, the at least one slit 68 of the septum 66 is forced open, breaking the seal, and fluid F may flow therethrough. The fluid F can be, for example, a saline solution or other IV-type of medical treatment solution. A coupler (not shown), such as a luer coupler, attached to a source of such IV fluid can be attached to the proximal flange 35. In some embodiments, the coupler can be configured so that, when it is attached, it forces the septum activator 100 distally so as to open the slit as discussed above.

Fluid F that is delivered through the septum 66 flows into the elongated distal tube 70, through the distal flow passage 74 and further into the catheter tube 30 for delivery to the patient's blood vessel. Such flow F will tend to displace the flashback blood B and carry it back into the patient's blood vessel, effectively flushing the blood B from the catheter hub 22. Again, however, preferably the hydrophobic porous layer 90 prevents both blood B and IV fluid F from flowing through the side apertures 76 and into the distal side chamber 80.

Figure 4:
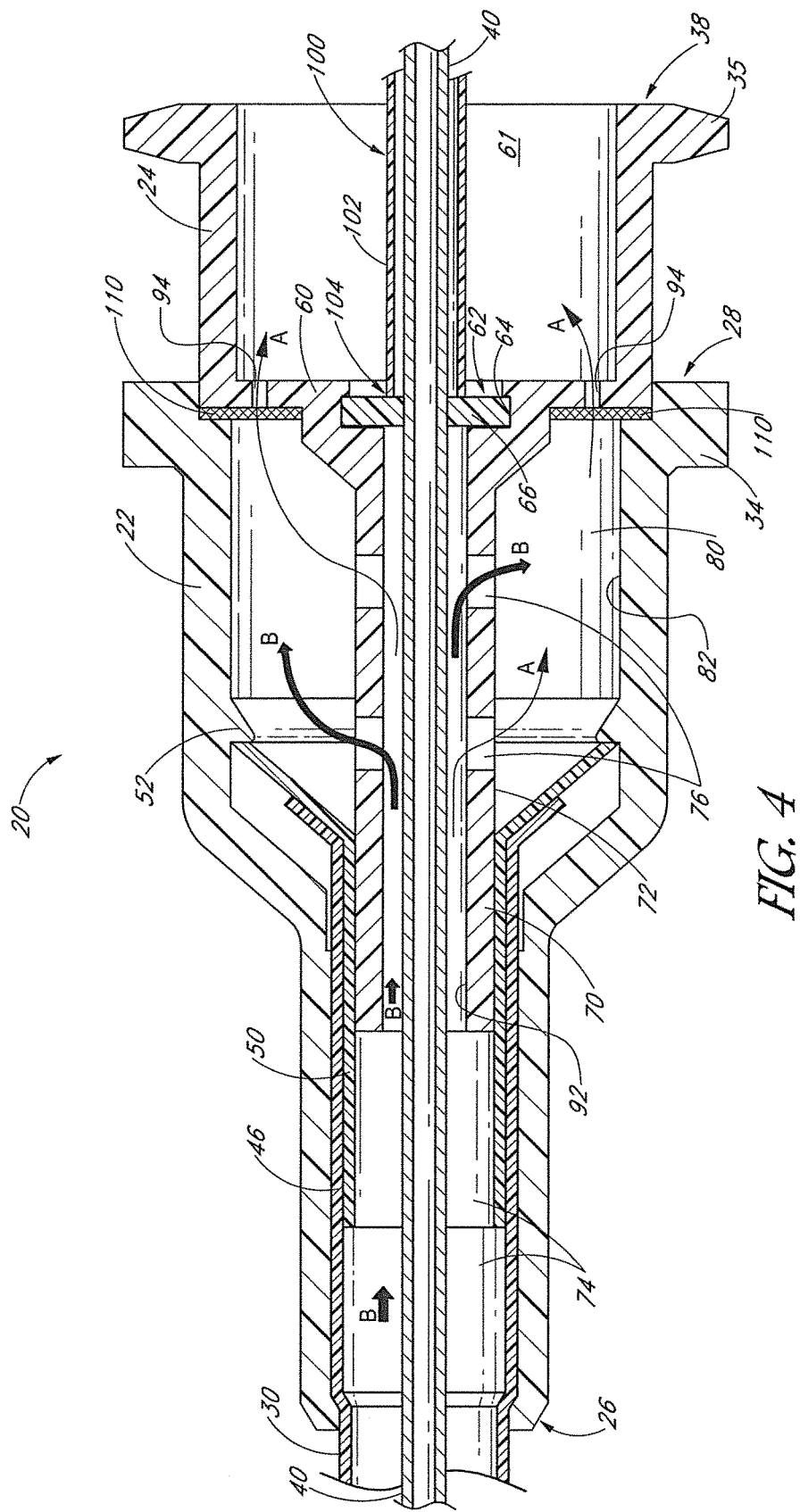
FIG. 4 is a cross-sectional view of another embodiment.

With reference next to FIG. 4, another embodiment is structurally similar to the embodiments discussed above in connection with FIGS. 2-3. However, in the illustrated embodiment, there is no hydrophobic porous layer in the elongated distal tube to block blood B from flowing through the side apertures 76 and into the distal side chamber 80. However, preferably an air-permeable, hydrophobic mesh layer 110 is disposed on a distal face of the central wall 60 so as to cover the air vents 94. As such, blood B within the distal side chamber 80 is blocked from flowing through the air vents 94, but air A flows readily through the hydrophobic mesh layer 110, through the air vents 94 and into the proximal chamber 61. In this manner air from within the catheter hub 22 is permitted to vent from the catheter hub 22 so as to prevent air pressure from unacceptably rising when flashback blood B is attempting to flow into the catheter hub 22.

Figure 5:
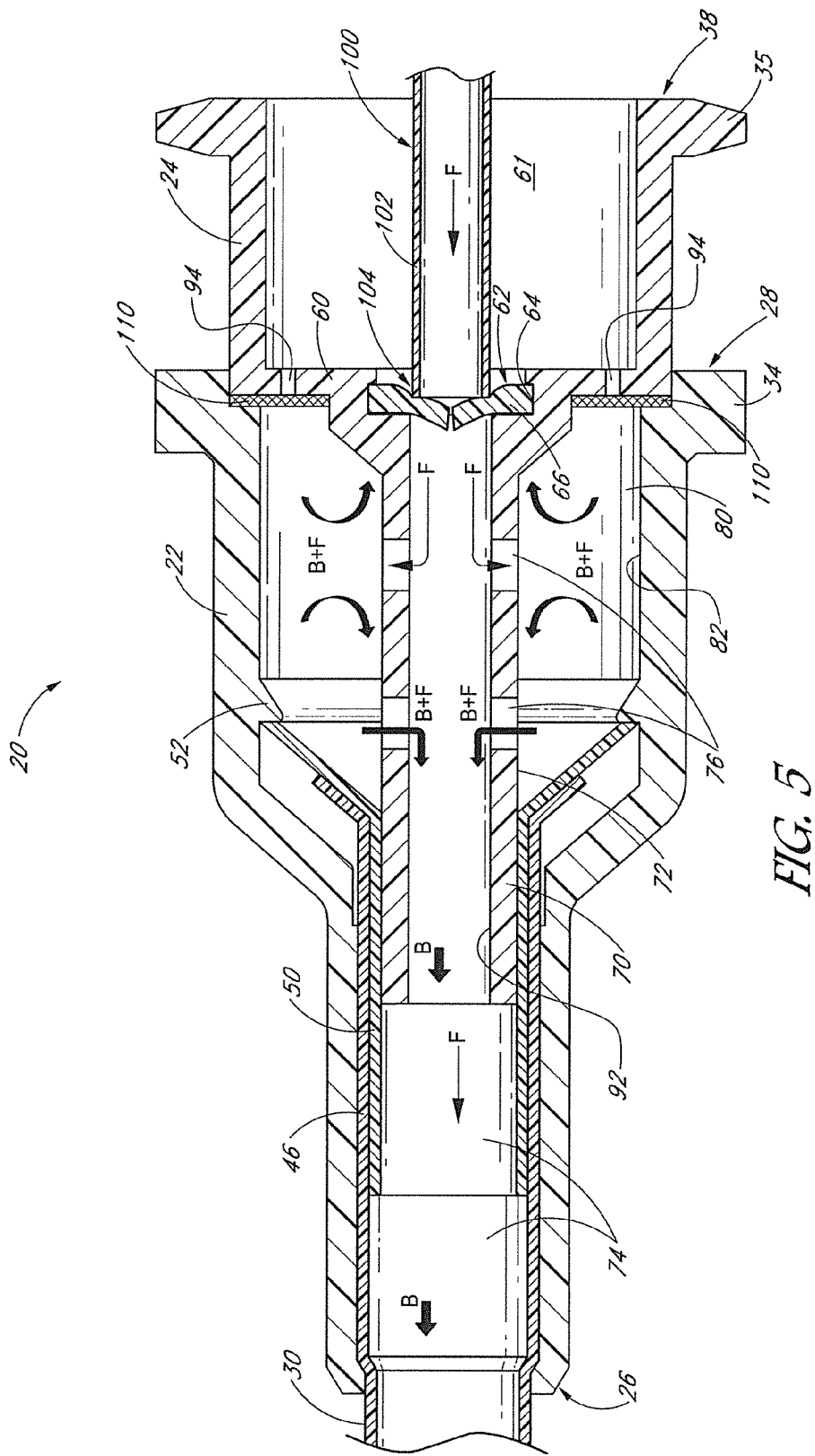
FIG. 5 is shows the assembly of FIG. 4 with the needle withdrawn and IV fluid being delivered.

With additional reference to FIG. 5, after flashback blood B has entered the catheter hub 22, verifying proper placement of the catheter tube, the needle 40 can be withdrawn, and the septum activator 100 can be moved distally sufficient to break the seal of the septum 66. IV fluid F is then delivered into the elongated distal tube 70 so as to flush blood B out of the catheter hub 22. Preferably, at least a portion of the fluid F flows through the side apertures 76 and into the distal side chamber 80, where the fluid F mixes with blood B in the chamber. The fluid F/blood B mixture eventually flows through the side apertures 76 and back into the elongated distal tube 70, from which it flows into the distal flow passage 74 and on to the catheter tube 30 and into the patient. Eventually blood B is substantially flushed from the entire catheter hub 22.

Figure 6:
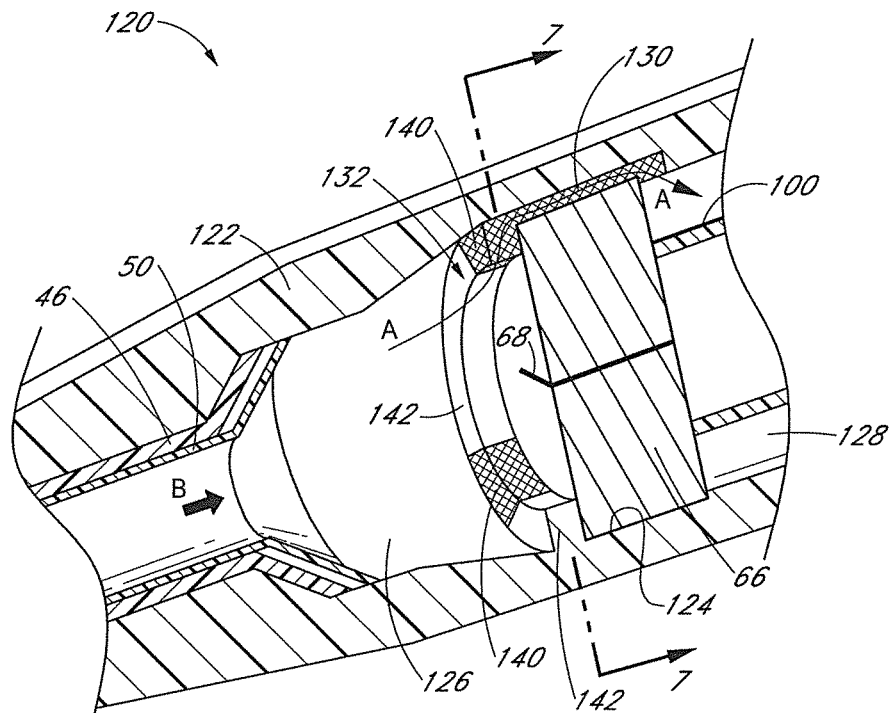
FIG. 6 is a cross-sectional view of yet another embodiment.
Figure 7:
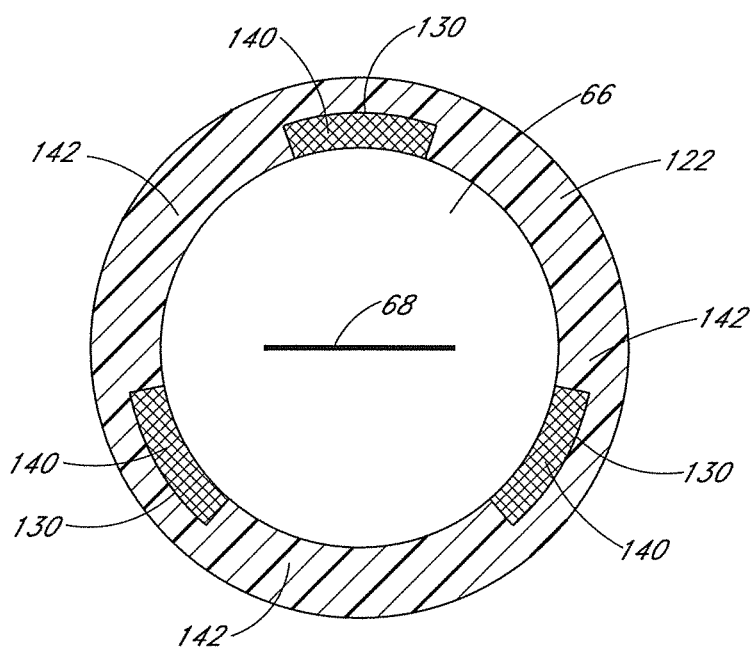
FIG. 7 is a cross-sectional view taken along lines 7-7 of FIG. 6.

With reference next to FIGS. 6-7, another embodiment of a catheter adapter 120 comprises an elongated unitarily-formed body 122. The catheter adapter 120 includes a catheter base 46 and retainer 50 so as to support and hold a catheter tube. An elastomeric septum 66 is sealingly received into a septum seat 124 formed in the body 122. A distal chamber 126 is defined within the catheter adapter 120 distal of the septum 66, and a proximal chamber 128 is defined proximal of the septum 66.

As shown in FIG. 6, the septum 66 rests against a distal end 132 of the septum seat 124. However a plurality of vent channels 130 are formed in the body 122, extending through the distal portion 132 of the septum seat 124, then along the side of the septum seat 124 and communicating with the proximal chamber 128. As such, the vent channels 130 communicate the distal chamber 126 with the proximal chamber 128. In the illustrated embodiment, the vent channels 130 are filled with a hydrophobic porous material 140 that enables air A to flow therethrough but repels water-based substances such as blood B. Thus, as shown in FIG. 6, flashback blood B flowing into the catheter adapter 22 distal chamber 126 can displace air A within the distal chamber 126, which air A will flow through the vent channels, passing through the hydrophobic porous material 140 that fills the vent channels 130, and into the proximal chamber 128. However, blood B will be blocked by the hydrophobic porous material 140 from entering the vent channels 130.

In the illustrated embodiment, three vent channels 130 are formed in the body 122. Spaces between the vent channels 130, such as the spaces 142 in the distal portion 132 of the septum seat as depicted in FIG. 7, can be solid, preferably being unitarily formed with the rest of the body 122.

As with embodiments discussed above, a septum activator 100 can be advanced distally so as to deform the septum 66 and open passageways through the slit 68 so that IV fluids can be delivered to flush the blood B out of the catheter adapter 122 and back into the patient's blood vessel.

Although inventive subject matter has been disclosed in the context of certain preferred or illustrated embodiments and examples, it will be understood by those skilled in the art that the inventive subject matter extends beyond the specifically disclosed embodiments to other alternative embodiments and/or uses of the invention and obvious modifications and equivalents thereof. For example, a method of making a catheter assembly as described herein, as well as a method of using such an assembly, is contemplated. In addition, while a number of variations of the disclosed embodiments have been shown and described in detail, other modifications, which are within the scope of the inventive subject matter, will be readily apparent to those of skill in the art based upon this disclosure. It is also contemplated that various combinations or subcombinations of the specific features and aspects of the disclosed embodiments may be made and still fall within the scope of the inventive subject matter. Accordingly, it should be understood that various features and aspects of the disclosed embodiments can be combined with or substituted for one another in order to form varying modes of the disclosed inventive subject matter. Thus, it is intended that the scope of the inventive subject matter herein disclosed should not be limited by the particular disclosed embodiments described above, but should be determined only by a fair reading of the claims that follow.

What is claimed is:

1. A catheter assembly, comprising:
a catheter adapter having a distal end and a proximal end;
an elongated catheter tube extending from the catheter adapter distal end;
a distal chamber and a proximal chamber defined within the catheter adapter, the distal chamber communicating with the catheter tube;
a divider interposed between the distal chamber and the proximal chamber;
one or more vent channels extending between the distal chamber and the proximal chamber so as to communicate the distal chamber with the proximal chamber; and
a hydrophobic porous material interposed between the distal chamber and the one or more vent channels, the hydrophobic porous material configured to allow air to pass therethrough so that air from the distal chamber can flow through the one or more vent channels to the proximal chamber, the hydrophobic porous material configured to repel blood so that blood within the distal chamber is prevented from flowing through the one or more vent channels.

2. A catheter assembly as in claim 1, wherein the one or more vent channels are formed through the divider.

3. A catheter assembly as in claim 2, wherein the divider comprises a central wall comprising an aperture, and a septum seat is defined about the aperture, an elastomeric septum being received within the septum seat so as to maintain a seal with the central wall, and wherein the one or more vent channels are formed through the central wall.

4. A catheter assembly as in claim 3 additionally comprising a distal tube extending distally from the central wall and defining a fluid flow passage within the distal chamber, a distal side chamber being defined between an outer surface of the distal tube and an inner surface of the catheter adapter, side apertures formed through a wall of the distal tube communicating the fluid flow passage with the distal side chamber.

5. A catheter assembly as in claim 4, wherein the side apertures through the wall of the distal tube are open for both air and fluid to flow into the distal side chamber.

6. A catheter assembly as in claim 5, wherein the hydrophobic porous material is applied to a distal side of the central wall so as to cover a distal opening of the one or more vent channels.

7. A catheter assembly as in claim 6, wherein the side apertures through the wall of the distal tube comprise a proximal side aperture and a distal side aperture, the distal side aperture being spaced distally from the proximal side aperture.

8. A catheter assembly as in claim 1, wherein the divider comprises an elastomeric septum.

9. A catheter assembly as in claim 8, wherein the one or more vent channels are formed in a body portion of the catheter adapter, the one or more vent channels being at least partially filled with the hydrophobic porous material.

* * * * *

UNITED STATES PATENT AND TRADEMARK OFFICE
CERTIFICATE OF CORRECTION

| | | |
|---|---|---|
| PATENT NO. | : 9,717,887 B2 | Page 1 of 1 |
| APPLICATION NO. | : 14/550423 | |
| DATED | : August 1, 2017 | |
| INVENTOR(S) | : Soo Yong Tan | |

It is certified that error appears in the above-identified patent and that said Letters Patent is hereby corrected as shown below:

In the Specification

In Column 4, Lines 64-65, delete "polyvinyldiflouride" and insert -- polyvinyldifluoride --, therefor.

Signed and Sealed this
Eleventh Day of December, 2018

Andrei Iancu
*Director of the United States Patent and Trademark Office*